United States Patent [19]

Cherkofsky

[11] 4,199,592
[45] Apr. 22, 1980

[54] ANTIINFLAMMATORY 4,5-DIARYL-2-NITROIMIDAZOLES

[75] Inventor: Saul C. Cherkofsky, Wilmington, Del.

[73] Assignee: E. I. Du Pont de Nemours and Company, Wilmington, Del.

[21] Appl. No.: 18,023

[22] Filed: Mar. 6, 1979

Related U.S. Application Data

[63] Continuation-in-part of Ser. No. 937,715, Aug. 25, 1978, abandoned.

[51] Int. Cl.² ............... C07D 233/91; A61K 31/415
[52] U.S. Cl. .................... 424/273 R; 548/336; 548/340; 546/278; 424/263
[58] Field of Search ............... 548/336, 339, 340; 424/273 R

[56] References Cited

U.S. PATENT DOCUMENTS

| | | | |
|---|---|---|---|
| 3,505,350 | 4/1970 | Doebel | 548/317 |
| 3,651,080 | 3/1972 | Doebel | 424/273 R |
| 3,707,475 | 12/1972 | Lombardino | 548/336 |
| 3,901,908 | 8/1975 | Fitzi et al. | 424/275 |
| 3,929,807 | 12/1975 | Fitzi | 546/278 |
| 3,954,789 | 4/1976 | Cavalleri | 548/339 |

OTHER PUBLICATIONS

Cherkofsky et al., Chem. Abst. 87, 1977, No. 5974b.
Zauer et al., Chem. Ber. 1973, vol. 106, pp. 1628–1636.
Bhatt et al., Current Science, India, 1948, vol. 17, pp. 184–185.

Primary Examiner—Alan L. Rotman
Assistant Examiner—Natalia Harkaway

[57] ABSTRACT

Antiinflammatory 4,5-diaryl-2-nitroimidazoles, such as 4,5-bis(4-fluorophenyl)-2-nitroimidazole, useful for treating arthritis and related diseases.

27 Claims, No Drawings

ANTIINFLAMMATORY 4,5-DIARYL-2-NITROIMIDAZOLES

CROSS REFERENCE TO RELATED APPLICATIONS

This application is a continuation-in-part of Ser. No. 937,715, filed Aug. 25, 1978, now abandoned.

BACKGROUND OF THE INVENTION

This invention relates to antiinflammatory imidazoles.

Lombardino, in U.S. Pat. No. 3,707,475 discloses antiinflammatory 4,5-diaryl-2-substituted imidazoles.

Doebel, in U.S. Pat. Nos. 3,505,350 and 3,651,080, respectively, discloses antiinflammatory 4-alkyl-5-aryl-1-substituted-2-mercaptoimidazoles and 4-alkyl-2-alkylthio-5-aryl-1-substituted-imidazoles.

Zauer, K., et al., in *Chem. Ber.*, 106, 1638 (1973) disclose 4,5-bis(4-methoxyphenyl)-2-methylthioimidazole and 4,5-bis(4-chlorophenyl)-2-methylthioimidazole but do not suggest any use.

A number of references, such as *Current Sci. India*, 17, 184-85 (1948) and *Acta. Chem. Acad. Sci. Hung.*, 79 (2) 197-212 (1973) disclose 2-(substituted-thio)-4,5-diphenylimidazoles with substituents such as methyl, propyl, allyl, and acetonyl.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new anti-arthritic compounds with good antiinflammatory activity and minimal side effects that could be more effective in treating arthritis than presently available drugs.

In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

According to this invention there is provided compounds of formula I, pharmaceutical compositions containing them, and methods of using them to treat arthritis in mammals.

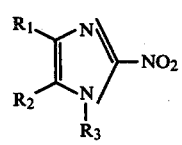
(I)

where
$R_1$ and $R_2$ independently are

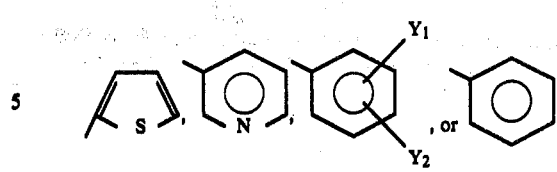

with the proviso at least one of $R_1$ and $R_2$ must be

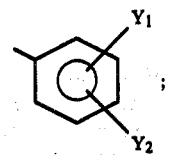

$Y_1$ is F, Cl, N(CH$_3$)$_2$ or C$_1$-C$_4$ alkoxy;
$Y_2$ is H, F, Cl;
$R_3$ is H,

2-tetrahydropyranyl, 2-tetrahydrofuranyl,

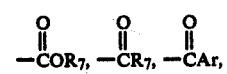

or —SO$_2$Ar;
$R_5$ is H or methyl;
$R_6$ is C$_1$-C$_3$ alkyl, benzyl, —CH$_2$CH$_2$OCH$_3$ or

$R_7$ is C$_1$-C$_4$ alkyl or benzyl; and
Ar is

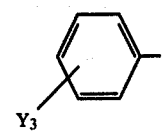

where $Y_3$ is H, F, Cl, Br, C$_1$-C$_4$ alkyl, C$_1$-C$_4$ alkoxy or nitro; or its pharmaceutically suitable acid addition salt where at least one of $R_1$ and $R_2$ is 3-pyridyl, or

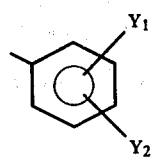

where
$Y_1$ is N(CH$_3$)$_2$;
or its pharmaceutically suitable metal salt where $R_3$ is H.

Some of the compounds of formula I have analgesic activity in addition to antiinflammatory activity.

Pharmaceutical Salts

Pharmaceutically suitable acid addition salts of compounds where one of $R_1$ and $R_2$ is 3-pyridyl and/or

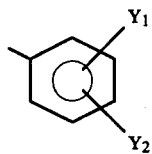

where
$Y_1$ is $N(CH_3)_2$ include those made with physiologically acceptable acids and such salts include hydrochloride, sulfate, phosphate and nitrate.

Pharmaceutically suitable metal salts where $R_3$ is H include those of certain metals, such as sodium, potassium, and calcium.

DETAILED DESCRIPTION OF THE INVENTION

Preferred Compounds

Compounds preferred for antiinflammatory activity are those where; independently:

(a) $R_1$ and $R_2$ are independently

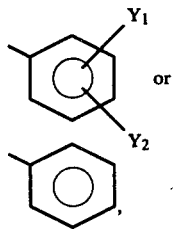

and more preferably

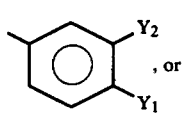

(b) where either $R_1$ or $R_2$ is

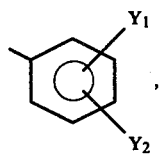

$Y_1$ is F, Cl, or $OCH_3$, and more preferably this constituent is in the para-position; and $Y_2$ is H; or (c) $R_3$ is H.

Examples of suitable compounds are where $R_1$ and $R_2$ are both

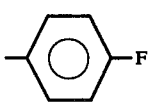

and $R_3$ is H; and
$R_1$ and $R_2$ are both

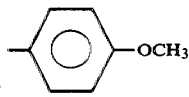

and $R_3$ is H.

Synthesis

Compounds of formula I can be prepared by first reacting a 4,5-disubstituted imidazole (II) with an appropriate reagent such as benzyl chloromethyl ether, 2-chlorotetrahydrofuran, dihydropyran, benzenesulfonyl chloride, or ethyl vinyl ether (Equation A). The resulting 4,5-disubstituted-1-(substituted)imidazole (III) is then treated with a strong base, such as n-butyl lithium, followed by dinitrogen tetroxide or some other suitable nitrating agent, such as acetyl nitrate or alkyl nitrates (Equation B). Optionally, the choice of the protecting group and the workup conditions allows isolation of a desired 4,5-disubstituted-2-nitroimidazole (I, $R_3 = H$) directly.

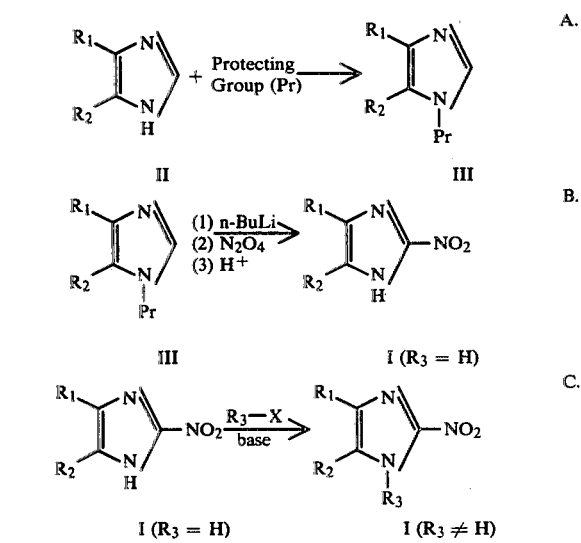

Alternatively, the $R_3$-substituent other than hydrogen of formula I can be introduced by direct alkylation, acylation, or sulfonylation of the compounds of formula I where $R_3 = H$ (Equation C). This reaction can be carried out in the absence or presence of a base, such as potassium carbonate, pyridine, triethylamine, potassium t-butoxide, methyllithium or the like. The reaction can be run neat, using the reagent as solvent, or in the presence of an inert solvent, including but not limited to dimethylformamide, glyme, THF, pyridine, methylene chloride. The temperature of the reaction can be in the range $-78°$ C. to the boiling point of the solvent or reagent, if used in excess as the solvent. Examples of alkylating, acylating and sulfonylating agents that can be employed are alkoxymethyl halides, such as benzyloxymethyl chloride; acyloxymethyl halides, such as chloromethylpivalate; dihydropyran; 2-chlorotetrahydrofuran; alkyl chloroformates, such as ethyl chloroformate; alkanoic anhydrides and alkanoyl halides, such as acetic anhydride; aroyl halides, such as benzoyl chloride; and arylsulfonyl halides, such as benzenesulfonyl chloride.

The 4,5-disubstituted imidazoles of formula II are commercially available or may be prepared by techniques well known to those skilled in the art, e.g. H. Bredereck, et al., Ber., 86, 88 (1953) and Ber., 92, 338 (1959).

Preparation of pharmaceutically suitable salts of formula I can be in accordance with well-known techniques of forming salts.

The preparation of these compounds is further illustrated by the following Examples. Parts are by weight and temperatures are in degrees centigrade unless otherwise stated.

EXAMPLE 1

4,5-bis(4-Fluorophenyl)-2-nitroimidazole

A mixture of 124 g (0.484 mole) of 4,5-bis(4-fluorophenyl)imidazole, 84 g (1.0 mole) dihydropyran, 20 g boron trifluoride etherate and 1 l ethyl acetate was heated at reflux over a weekend. Analysis by TLC (ethyl acetate) showed the presence of some unchanged starting material, so 20 g (~0.24 mole) of dihydropyran and 5 g boron trifluoride etherate was added and heating was continued overnight. The mixture was then diluted with 1 l ether and washed with 10% sodium bicarbonate solution (3×1 l). The organic layer was dried and concentrated on a rotary evaporator. The residual solid was recrystallized from methylcyclohexane (removing some insoluble starting material by filtration) to give 140.2 g (85%) of 4,5-bis(4-fluorophenyl)-1-(2-tetrahydropyranyl)imidazole as a white solid, mp 149°–152°. F-NMR indicated purity ~95%. A smaller run was chromatographed to give pure material mp 158°–9°. IR: 3.25μ (=CH); 3.38, 3.49μ (sat. CH); 6.22, 6.28, 6.41, 6.60, 6.69μ (C=C and/or C=N); 8.20μ (CF); 9μ region (C—O—C). H-NMR: m(1.4–2.1 δ, 6H); m (3.4 δ,1H); m (4.0 δ, 1H); m (4.7 δ, 1H); m (6.6–7.5 δ, 8H); s (7.8 δ, 1H). F-NMR: two multiplets (112.4 δ and 116.5 δ, each decouples to a singlet).

To a mixture of 17.0 g (50 mmole) of 4,5-bis(4-fluorophenyl)-1-(2-tetrahydropyranyl)imidazole, 6.4 g (55 mmole) of N,N,N',N'-tetramethylenediamine and 200 ml of ether cooled to −78° was added dropwise 35 ml (55 mmole) of 1.6 M butyl lithium. After stirring for 15 minutes, a solution of 7.9 g (86 mmole) of dinitrogen tetroxide in 50 ml of ether was added dropwise. The reaction mixture was allowed to warm to room temperature and then was distributed between 5% aqueous sodium bicarbonate and ether. The ether was dried and evaporated to give 21.7 g of an amber oil.

The oil was heated with a mixture of 125 ml of ethanol and 10 ml of 1 N aqueous hydrochloric acid for a few minutes. The reaction mixture was concentrated under vacuum.

Chromatography and recrystallization of the product from toluene gave 6.1 g of 4,5-bis(4-fluorophenyl)-2-nitroimidazole, m.p. 245°–6° (dec.). The infrared, NMR and F-NMR spectra were consistent with the assigned structure.

Anal. Calc'd for $C_{15}H_9F_2N_3O_2$: C, 59.81; H, 3.01; N, 13.95. Found: C, 60.21; H, 3.03; N, 13.55.

EXAMPLE 2

4,5-bis(4-Methoxyphenyl)-2-nitroimidazole

By the procedure described in the first paragraph of Example 1, 4,5-bis(4-methoxyphenyl)imidazole was converted in 50% yield to 4,5-bis(4-methoxyphenyl)-1-(2-tetrahydropyranyl)imidazole, as a white solid, m.p. 123°–5°. IR: 3.26μ (=CH); 3.40, 3.53μ (sat. CH); 6.17, 6.32, 6.58, 6.68μ (C=C and/or C=N); 8.03μ (aryl-o); 9.60 and 9.72μ (C—O—C). H-NMR: m (1.3–2.1 δ, 6H); two singlets (3.75–3.85 δ, 6H); m (3.2–4.2 δ, 2H); ~t (4.85 δ, 1H); two A$_2$B$_2$ quartets (6.7–7.6 δ, 8H); s (7.85 δ, 1H).

Anal. Calc'd. for $C_{22}H_{24}N_2O_3$: C, 72.51; H, 6.64; N, 7.69. Found: C, 72.32; H, 6.35; N, 7.37.

By the procedure described in Example 1, 14.5 g of 4,5-bis(4-methoxyphenyl)-1-(2-tetrahydropyranyl)-imidazole was converted to 4,5-bis(4-methoxyphenyl)-2-nitroimidazole. Chromatography gave an analytical sample, m.p. 174° (dec.). The infrared and NMR spectra were consistent with the assigned structure.

Mass Calc'd for $C_{17}H_{15}N_3O_4$: 325.1062. Mass found: 325.1030.

EXAMPLE 3

4-(4-Fluorophenyl)-5-(2-thienyl)-2-nitroimidazole

To a mixture of 100.0 g. (0.65 mole) of 4-fluorophenylacetic acid and 260.0 g of thiophene warmed to 40° C. was added dropwise 150.0 g (0.71 mole) of trifluoroacetic anhydride. The reaction mixture was heated at reflux for 3 hours, cooled and then poured into ice. The aqueous layer was made basic with sodium carbonate and the product was extracted into ether. The combined ether extracts were washed with water and, after drying over anhydrous potassium carbonate, were evaporated to give 150.5 g of an oil. Crystallization from methanol afforded 94.1 g of 2-(4-fluorophenyl)-1-(2-thienyl)ethanone, m.p. 60°–61° C.

Anal. Calc'd for $C_{12}H_9FOS$: C, 65.45; H, 4.09; Found: C, 65.45; H, 4.06.

To a solution of 94.1 g (0.43 mole) of 2-(4-fluorophenyl)-1-(2-thienyl)ethanone in 700 ml. of ether was added dropwise a solution of 65.0 g. (0.41 mole of bromine in 140 ml. of methylene chloride at room temperature with stirring. The solvent was removed under vacuum to give 125.0 g of 2-bromo-2-(4-fluorophenyl)-1-(2-thienyl)ethanone.

A mixture of the 2-bromo-2-(4-fluorophenyl)-1-(2-thienyl)ethanone and 465 ml. of formamide was heated at reflux under an air condenser for 2 hours. The reaction mixture was allowed to cool to room temperature and 73.3 g of 4-(4-fluorophenyl)-5-(2-thienyl)imidazole, m.p. 182°–189° C., collected by filtration. An analytical sample was prepared by recrystallization from nitromethane, m.p. 200°–202° C. H-NMR: m (6.9–7.7δ, 7H); s (7.8δ, 1H).

Anal. Calc'd for $C_{13}H_9N_2FS$: C, 63.93; H, 3.69; N, 11.48. Found: C, 63.43; H, 3.82; N, 11,56.

By the procedure described in the first paragraph of Example 1, 35.0 g of 4-(4-fluorophenyl)-5-(2-thienyl)imidazole was converted to 56.6 g of 4(5)-(4-fluorophenyl)-5(4)-(2-thienyl)-1-(2-tetrahydropyranyl)imidazole. Chromatography on neutral alumina (Woelm activity Grade I) eluting with chloroform gave 30.0 g of pure material as a mixture of two isomers. H-NMR: m (1.4–2.1δ, 6H); m (3.3δ, 1 H); m(4.0δ, 1H); m (4.8δ, 1H); m (6.7–7.7δ, 7H); 2s (7.9, 1H).

By the procedure described in Example 1, 30.0 g of 4(5)-(4-fluorophenyl)-5(4)-(2-thienyl)-1-(2-tetrahydropyranyl)imidazole was converted to 4-(4-fluorophenyl)-5-(2-thienyl)-2-nitroimidazole. Purification was effected by dissolving the crude product in aqueous 0.2 M potassium hydroxide followed by filtration, then acidification with acetic acid to precipitate an analytical sample, mp. 177.5°–179° C. The infrared and NMR spectra were consistent with the assigned structure.

Mass Calc'd. for $C_{13}H_8FN_3O_2S$: 289;
Mass Found: 289.

Anal. Calc'd. for $C_{13}H_8FN_3O_2S$: C, 53.98; H, 2.77; N, 14.53. Found: C, 54.5; H, 2.84; N, 14.4.

EXAMPLE 4

4-(4-Ethoxyphenyl)-5-(4-fluorophenyl)-2-nitroimidazole

A mixture of 24.4 g (86.5 mmoles) of 4-(4-ethoxyphenyl)-5-(4-fluorophenyl)imidazole, 12.5 g (0.173 mole) of ethyl vinyl ether and 11.2 g (86.8 mmoles) of dichloroacetic acid in 175 ml. of toluene was heated at reflux for several hours. After cooling to room temperature, the reaction mixture was stirred overnight with 85 ml. of 20% aqueous sodium hydroxide. The toluene layer was separated, washed several times with water, dried over anhydrous potassium carbonate and then evaporated to give 21.6 g of 4(5)-(4-ethoxyphenyl)-5(4)-(4-fluorophenyl)-1-(1-ethoxyethyl)imidazole as an oil. The oil was chromatographed on neutral alumina (Woelm activity Grade I) eluting with chloroform to give 18.0 g of pure material. H-NMR: m (1.0–1.8δ, 9H); q (3.2δ, 2H); q (4.1δ, 2H); q (5.1δ, 1H); m (6.7–7.7δ, 8H); s(7.8δ, 1H).

By the procedure described in Example 1, 8.5 g of 4(5)-(4-ethoxyphenyl)-5(4)-(4-fluorophenyl)-1-(1-ethoxyethyl)imidazole was converted to 4-(4-ethoxyphenyl)-5-(4-fluorophenyl)-2-nitroimidazole. The infrared and NMR spectra were consistent with the assigned structure. Chromatography on Silica-AR with chloroform followed by recrystallization from 1-chlorobutane gave an analytical sample, mp 176° C. (dec.).

Mass Calc'd. for $C_{17}H_{14}N_3FO_3$: 327; Mass Found: 327.

Anal. Calc'd. for $C_{17}H_{14}N_3FO_3$: C, 62.39; H, 4.28; N, 12.84. Found: C, 62.4; H, 4.33; N, 12.6.

EXAMPLE 5

4-(3,4-Dichlorophenyl)-5-phenyl-2-nitroimidazole

A mixture of 4-(3,4-dichlorophenyl)-5-phenylimidazole (14.5 g, 50 mmole), ethyl vinyl ether (10 ml., 100 mmole) and dichloroacetic acid (4.2 ml., 50 mmole) in 100 ml. toluene was heated at reflux under $N_2$ for 1 hour. The cooled reaction mixture was treated with 50 ml. 20% aqueous NaOH, stirred overnight and then left to stand at room temperature for two days. The organic phase was washed with water, dried over $K_3CO_3$ and concentrated on a rotary evaporator to give 4(5)-(3,4-dichlorophenyl)-5(4)-phenyl 1-(1-ethoxyethyl)-imidazole as an oil.

H-NMR 1.13δ (t, J=7 Hz, 3H), 1.63δ (d, J=6 Hz, 3H), 3.3δ (2q, J=7 Hz, 2H), 5.13δ (q, J=6 Hz, 1H), 7.28–7.8δ (m, 8H), 7.91δ (s, 1H).

The resultant (5)-4-(3,4-dichlorophenyl)-5-(4)-phenyl-1-(1-ethoxyethyl)imidazole (50 mmole) and N,N,N',N'-tetramethylethylenediamine (7.5 ml., 55 mmole) in 200 ml. THF was cooled to −78° C. under $N_2$ and treated dropwise with 1.6 M n-butyllithium (41 ml. 65 mmole). After stirring for 15 minutes, a solution of dinitrogen tetroxide (7 ml., 110 mmole) in 25 ml. ether was added dropwise. The reaction mixture was stirred for 1 hour at and then allowed to warm to room temperature. The dark mixture was poured into 300 ml. saturated aqueous $NaHCO_3$ and extracted with ether. The combined organic extracts were washed with brine, dried and divided into two portions 3:1). The larger portion was concentrated on the rotary evaporator, redissolved in 125 ml. ethanol, treated with 30 ml 1 N HCl and heated at reflux for 10 minutes. The reaction mixture was cooled to room temperature and diluted with 35 ml. water. The crystals were collected, washed with 0.1 N KOH and recrystallized from methylene chloride to give 1.2 g of 4-(3,4-dichlorophenyl)-5-phenyl-2-nitroimidazole, mp. 248°–249° C. (D). Infrared and H-NMR spectra were consistent with the assigned structure. MS 333 (M+).

Anal. Calc'd. for $C_{15}H_9N_3O_2Cl_2$: C, 53.91; H, 2.71; N, 12.58; Found: C, 53.86; H, 2.54; N, 12.67.

EXAMPLE 6

4-(4-Fluorophenyl)-5-(3-pyridyl)-2-nitroimidazole

A mixture of 82.0 g (0.6 mole) of methyl nicotinate and 81.0 g (0.6 mole) of p-fluorobenzyl cyanide was added dropwise to a solution of 0.9 mole of sodium ethoxide in 250 ml. of ethanol at room temperature with stirring. The reaction mixture was heated at reflux overnight, cooled and then poured onto ice-water. The aqueous solution was washed with ether and then acidified with concentrated hydrochloric acid. A precipitate was collected by filtration and washed with water. A mixture of the solid with 350 ml. of 48% hydrobromic acid was heated at reflux overnight with stirring. The reaction solution was allowed to cool to room temperature and crystals were collected by filtration. The crystals were suspended in water which was then made basic with concentrated ammonium hydroxide. The product was extracted into ether, which, after drying over anhydrous potassium carbonate, was evaporated to afford 77.9 g of fluorobenzyl 3-pyridyl ketone as colorless crystals, mp. 64°–65° C. IR: 6.0 m (C=O). H-NMR: s(4.3δ, 2H); m (6.9–7.6δ, 5H); d/t (8.2, 1H); d/d (8.8δ, 1H); d (9.3δ, 1H).

To a solution of 15.0 g (69.8 mmoles), 4-fluorobenzyl 3-pyridyl ketone in 120 ml. of acetic acid was added dropwise a solution of 12.3 g (76.9 mmoles) of bromine in 120 ml. of acetic acid at room temperature with stirring. After stirring overnight, a precipitate of 18.4 g of α-bromo 4-fluorobenzyl 3-pyridyl ketone hydrobromide was collected by filtration.

A mixture of the α-bromo 4-fluorobenzyl 3-pyridyl ketone hydrobromide with 150 ml. of formamide was heated at reflux with an air condenser under nitrogen for 2 hours. The reaction mixture was allowed to cool to room temperature and then poured onto water. The aqueous solution was made basic with sodium carbonate and the product extracted into ether. The combined ether extracts were washed with a saturated aqueous sodium bicarbonate solution, dried over anhydrous potassium carbonate and evaporated to give 7.5 g of 4-(4-fluorophenyl)-5-(3-pyridyl)imidazole. The product was purified by chromatography on neutral alumina (Woelm activity Grade I) eluting with ethyl acetate/tetrahydrofuran mixtures and then crystallization with ether gave 2.2 g of pure imidazole, mp. 154°–156° C. H-NMR: m (6.8–7.58δ, 5H); s(7.6δ, 1H); d/t (7.8δ, 1H); d/d (8.4δ, 1H); d(8.7δ, 1H).

Anal. Calc'd. for $C_{14}H_{19}FN_3$: C, 70.29; H, 4.18; N, 17.57; Found: C, 70.3; H, 4.43; N, 18.0.

Alternatively, a mixture of 28.8 g of α-bromo 4-fluorobenzyl 3-pyridyl ketone hydrobromide and 40.0 g of potassium acetate in 50 ml of acetic anhydride was stirred overnight at room temperature. The reaction mixture was poured into water and the product extracted into ether. The combined ether layers were washed with water and then 10% aqueous sodium bicarbonate solution. The ether layer was dried over potassium carbonate and evaporated. A solution of the residue in 250 ml. of 1 N aqueous hydrochloric acid was heated at reflux for 30 minutes, and after cooling, made basic with solid sodium carbonate. The product was extracted into ether and the combined ether extracts evaporated, after drying over anhydrous potassium carbonate, to give 16.5 g of α-hydroxy 4-fluorobenzyl 3-pyridyl ketone.

The 16.5 g of α-hydroxy 4-fluorobenzyl 3-pyridyl ketone was reacted with 12.5 g of ammonium thiocyanate in 1-propanol heated at reflux to give 11.3 g of 4-(4-fluorophenyl)-5-(3-pyridyl)-1H-2-imidazolethiol, mp. 335°-338° (dec.).

4-(4-Fluorophenyl)-5-(3-pyridyl)-1H-2-imidazolethiol (8.2 g) was added portionwise to a mixture of 30 ml. of 35% nitric acid at room temperature. After stirring overnight, the reaction mixture was diluted with water and made basic with sodium carbonate. The product was extracted into ethyl acetate, which, after drying over potassium carbonate was evaporated to yield 5.3 g of 4-(4-fluorophenyl)-5-(3-pyridyl)imidazole.

By the procedure described in the first paragraph of Example 4, 1.5 g of 4-(4-fluorophenyl)-5-(3-pyridyl)imidazole was converted to 4(5)-(4-fluorophenyl)-5(4)(3-pyridyl)-1-(1-ethoxyethyl)imidazole. Chromatography on neutral alumina (Woelm activity Grade I) eluting with tetrahydrofuran gave pure material. H-NMR: t(1.2δ, 3H); d (1.6δ, 3H); m (3.0–3.4δ, 2H); q (5.1δ, 1H); M (6.8–7.5δ, 5H); t (7.7δ, 1H); s (7.8δ, 1H); d/d (8.4δ, 1H); d(8.7, 1H).

By the procedure described in Example 1, 1.0 g of 4(5)-(4-fluorophenyl)-5(4)(3-pyridyl(1-ethoxyethyl)imidazole was converted to 4-(4-fluorophenyl)-5-(3-pyridyl)-2-nitroimidazole. Rf=0.19 [TLC; silica gel G; ethyl acetate: methanol (90:10)].

EXAMPLE 7

1-Benzoyl-4,5-bis(4-methoxyphenyl)-2-nitroimidazole

To a solution of 4,5-bis(4-methoxyphenyl)-2-nitroimidazole (3 g, 9.2 mmole) and triethylamine (3.9 ml., 27.6 mmole) in 30 ml. THF at 0° C. under $N_2$ was dropwise added a solution of benzoyl chloride (1.2 ml., 10.1 mmole) in 5 ml THF. The reaction mixture was stirred for 8 hours at 0° C. and then left in the refrigerator overnight. The reaction was then diluted with 30 ml ether and filtered. The filtrate was concentrated on a rotary evaporator and chromatographed on Florisil. Recrystallization from methylcyclohexane gave 1.89 g of 1-benzoyl-4,5-bis(4-methoxyphenyl)-2-nitroimidazole, mp. 161°-163° C.

IR: 1745 cm$^{-1}$, H-NMR: 3.73δ (s, 3H), 3.75δ (s, 3H), 6.67-7.83δ (m, 13H), MS 429 (M+)

Anal. Calc'd. for $C_{24}H_{19}N_3O_5$: C, 67.12; H, 4.46; N, 9.7; Found: C, 67.2; H, 4.40; N, 9.5.

EXAMPLE 8

1-Ethoxycarbonyl 4,5-bis(4-methoxyphenyl)-2-nitroimidazole

To a solution of 4,5-bis(4-methoxyphenyl)-2-nitroimidazole (1.5 g, 4.6 mmole) in 25 ml pyridine at 0° C. under nitrogen was dropwise added ethyl chloroformate (1.5 ml. 156 mmole). After 5 hours at 0° C., the reaction mixture was diluted with ethyl acetate, washed 3×1 N HCl, 3×saturated $NaHCO_3$, 1×brine, dried and concentrated on a rotary evaporator. Chromatography on Florsil gave 487 mg. of 1-ethoxycarbonyl-4,5-bis(4-methoxyphenyl)-2-nitroimidazole as an oil. IR 1795 cm$^{-1}$. H-NMR: 1.21δ(t, J=7 Hz, 3H), 3.7δ(s, 3H), 3.8δ(s, 3H), 4.3δ(q, J=7 Hz, 2H), 6.6-7.76 δ(2 AB quartets, J=8 Hz, 8H); MS 397 (M+).

EXAMPLE 9

1-Acetyl-4,5-bis(4-methoxyphenyl)-2-nitroimidazole

To a solution of 4,5-bis(4-methoxyphenyl)-2-nitroimidazole (3.0 g, 9.22 mmole) and triethylamine (7 ml., 51 mmole) in 30 ml. THF at 0° C. under $N_2$ was dropwise added a solution of acetyl chloride (1.3 ml., 18.4 mmole) in 5 ml. THF. After 2 hours at 0° C., the reaction mixture was diluted with ethyl acetate washed with 1 N HCl, saturated aqueous $NaHCO_3$ and brine, dried and concentrated on a rotary evaporator. Crystallization from ether gave approximately 600 mg. of starting material. HPLC of the mother liquor and crystallization from ether gave 1-acetyl 4,5-bis(4-methoxyphenyl)-2-nitroimidazole, mp. 146°-151° C. H-NMR indicates purity >95%. H-NMR: 2.41δ(s, 3H), 3.8δ(s, 3H), 6.73-7.56 δ(2 AB quartets, J=9 Hz, 8H).

EXAMPLE 10

1-(1-Ethoxyethyl)-4,5-bis(4-methoxyphenyl)-2-nitroimidazole

A mixture of 4,5-bis(4-methoxyphenyl)-2-nitroimidazole (1 g, 308 mmole), ethylvinyl ether (1 ml., 6.16 mmole) and dichloroacetic acid (0.3 ml, 3.08 mmole) in 10 ml. toluene was heated at reflux under $N_2$ for 1 hour. The reaction mixture was cooled, 2 ml. ethyl vinyl ether added and heating continued overnight. The cooled reaction mixture was treated with 5 ml. 20% NaOH and stirred 24 hours. The organic phase was washed with water, and brine, dried over $K_2CO_3$ and concentrated on a rotary evaporator. Chromatography on Florisil gave 178 mg. 1-(1-ethoxyethyl)-4,5-bis(4-methoxyphenyl)-2-nitroimidazole as an oil. H-NMR: 1.08δ(t, J=7H$_2$, 3H), 1.65δ (d, J=6H$_2$, 3H), 3.4δ(q, J=7H, 2H); 3.73δ(S, 3H), 3.86δ(S, 3H), 5.9δ(q, J=6H$_2$, 1H), 6.6–7.36δ (2 AB quartets, 8H), MS 352 (M—OC$_2$H$_5$), 325 (M—C$_2$H$_3$OC$_2$H$_5$).

Other compounds that can be prepared by using the appropriate starting materials and the procedures described in the examples and in the Synthesis section are illustrated in the following table.

TABLE I

| $R_1$ | $Y_1$ | $Y_2$ | $R_3$ |
|---|---|---|---|
| (3-pyridyl) | 4-Cl | H | H |
| (2-thienyl) | 4-F | H | —CHOC$_2$H$_5$ <br> \| <br> CH$_3$ |

TABLE I-continued

Structure: imidazole with $R_1$, $NO_2$, phenyl with $Y_1$, $Y_2$, and $R_3$ on N.

| $R_1$ | $Y_1$ | $Y_2$ | $R_3$ |
|---|---|---|---|
| 3-pyridyl | 4-F | H | tetrahydropyran-2-yl |
| phenyl | 4-F | H | H |
| phenyl | 3-Cl | 4-Cl | H |
| 2-thienyl | 3-Cl | 4-Cl | H |
| 3-pyridyl | 3-Cl | 4-Cl | H |
| 2-thienyl | 4-OCH₃ | H | H |
| 3-pyridyl | 4-OCH₃ | H | H |
| phenyl | 4-OCH₃ | H | H |
| 4-F-phenyl | 4-OCH₃ | H | —CO₂CH₂—phenyl |
| 4-F-phenyl | 4-N(CH₃)₂ | H | H |
| 4-Cl-phenyl | 4-OCH₃ | H | —CO—phenyl |
| phenyl | 4-OC₂H₅ | H | —COCH₃ |
| 4-F-phenyl | 4-OC₂H₅ | H | tetrahydrofuran-2-yl |
| 4-OCH₃-phenyl | 3-Cl | 4-Cl | —CH₂OCH₂—phenyl |
| 4-F-phenyl | 3-Cl | 4-Cl | —SO₂—phenyl |
| 4-N(CH₃)-phenyl | 3-Cl | 4-Cl | H |
| 2,3-Cl₂-phenyl | 3-Cl | 4-Cl | H |
| 2-thienyl | 4-Cl | H | H |
| phenyl | 3-Cl | 4-Cl | —CH₂OC(O)—C(CH₃)₃ |
| 4-F-phenyl | 4-F | H | —CHOC₂H₅ \| CH₃ |
| 4-OCH₃-phenyl | 4-OCH₃ | H | —CHOC₂H₅ \| CH₃ |
| 4-F-phenyl | 4-F | H | —SO₂—phenyl—Cl |

Dosage Forms

The anti-arthritic and analgesic agents of this invention can be administered to treat arthritis and/or pain by any means that produces contact of the active agent with the agent's site of action in the body of a mammal. The compounds of formula I have anti-arthritic properties and in addition some can be used to alleviate pain. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.1 to 50 and preferably 1.0 to 25 milligrams per kilogram per day given in divided doses 2 to 4 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a Standard reference test in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Capsules

A mixture of active ingredient in soybean oil is prepared and injected by means of a positive displacement pump into geletin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 275 milligrams of lactose. Appropriate coatings may be applied to increase palatability or delay absorption.

Injectable

A parenteral composition suitable for adminstration by injection is prepared by stirring 1.5% by weight of active ingredient in 10% by volume propylene glycol and water. The solution is sterilized by filtration.

Suspension

An aqueous suspension is prepared for oral adminintration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Use

To detect and compare the antiinflammatory activities of compounds in this series and standard drugs, a test was used based on a standard model of arthritis for which there is good correlation with human efficacy. The model is adjuvant-induced arthritis in rats. Federation Proceedings, Vol. 32, No. 2 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Nonarthritic controls are injected with mineral oil. The animals are held for two weeks to allow development of arthritis. Paw volumes (uninjected, left hind paw) are measured and the adjuvant injected rats are culled and distributed to treatment groups of 10 of equal disease severity. Nonarthritic controls are distributed to two groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the six following days. One day after the last dose the paw volumes (uninjected, left hind paw) are measured using a Ugo Basile Volume Differential Meter Model 7101.

$$\frac{\left(\begin{array}{c}\text{Arthritic Control}\\ \text{Mean Paw Volume (ml)}\end{array}\right) - \left(\begin{array}{c}\text{Treatment Group}\\ \text{Mean Paw Volume (ml)}\end{array}\right)}{\left(\begin{array}{c}\text{Arthritic Control}\\ \text{Mean Paw Volume (ml)}\end{array}\right) - \left(\begin{array}{c}\text{Non-Arthritic Control}\\ \text{Mean Paw Volume (ml)}\end{array}\right)} \times$$

100 = % Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Table II.

Compounds from this series were also compared to indomethacin, phenylbutazone, ibuprofen, and aspirin.

TABLE II

| Established Adjuvant-Induced Arthritis in Rats (A.A.) | |
|---|---|
| Chemical Example Number | A.A. ED50% mg/kg |
| 1 | 0.6 (1.3) |
| 2 | 2.5 |
| Indomethacin | 0.3 |
| Phenylbutazone | 10 |
| Ibuprofen | 100 |
| Aspirin | 305 |

Phenylquinone Writhing Test

A standard procedure for detecting and comparing the analgesic activity of compounds in this series for which there is good correlation with human efficacy is the standard phenylquinone writhing test modified from Siegmund, et al., *Proc. Soc. Exp. Biol. Med.* 95, 729 (1957). A test compound suspended in 1% methylcellulose was given orally to fasted (17-21 hours) female white mice, 5-20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.* 11, 115-145 (1947); also time of peak action was determined for many of the compounds. This data is summarized in Table III.

TABLE III
Phenylquinone Writhing Test

| Chemical Example Number | $ED_{50}$* |
|---|---|
| 1 | 59 (30) |
| 2 | <130 |

*units are in mg/kg at ½ hour.

"Consisting essentially of" in the present specification is intended to have its customary meaning: namely, that all specified materials and conditions are very important in practicing the invention but that unspecified materials and conditions are not excluded so long as they do not prevent the benefits of the invention from being realized.

What is claimed is:

1. A compound of the formula

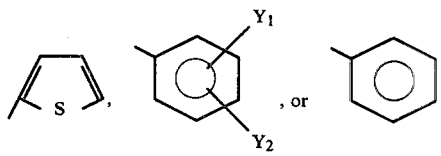

where $R_1$ and $R_2$ independently are

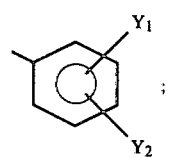

with the proviso at least one of $R_1$ and $R_2$ must be

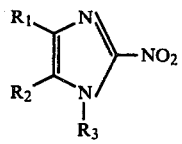

$Y_1$ is F, Cl, N(CH$_3$)$_2$ or $C_1$-$C_4$ alkoxy;
$Y_2$ is H, F, Cl;
$R_3$ is H,

2-tetrahydropyranyl, 2-tetrahydrofuranyl,

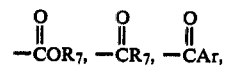

or —SO$_2$Ar;
$R_5$ is H or methyl;
$R_6$ is $C_1$-$C_3$ alkyl, benzyl, —CH$_2$CH$_2$OCH$_3$ or

$R_7$ is $C_1$-$C_4$ alkyl or benzyl; and
Ar is

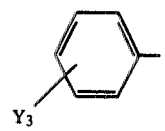

where
$Y_3$ is H, F, Cl, Br, $C_1$-$C_4$ alkyl, $C_1$-$C_4$ alkoxy or nitro; or
a pharmaceutically suitable acid addition salt thereof where at least one of $R_1$ and $R_2$ is

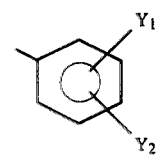

where
$Y_1$ is N(CH$_3$)$_2$,
or a pharmaceutically suitable metal salt thereof where $R_3$ is H.

2. A compound of claim 1 where $R_1$ and $R_2$ are independently

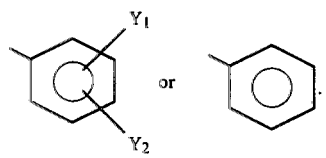

3. A compound of claim 1 where $R_1$ or $R_2$ is

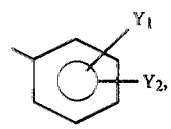

$Y_1$ is F, Cl, or OCH$_3$, and $Y_2$=H.

4. A compound of claim 3 where $Y_1$ is in the para-position.

5. A compound of claim 1 where $R_3$ is H.

6. A compound of claim 2 where $R_1$ or $R_2$ is

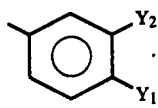

7. A compound of claim 4 where
$Y_1$ is F, Cl or $OCH_3$;
$Y_2$ is H; and
$R_3$ is H.
8. The compound of claim 1 where $R_1$ and $R_2$ are both

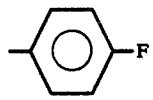

and $R_3$ is H.
9. The compound of claim 1 where $R_1$ and $R_2$ are both

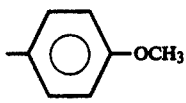

and $R_3$ is H.
10. A pharmaceutical composition consisting essentially of a suitable pharmaceutical carrier and an effective antiinflammatory amount of a compound of claim 1.
11. A pharmaceutical composition consisting essentially of a suitable pharmaceutical carrier and an effective antiinflammatory amount of a compound of claim 2.
12. A pharmaceutical composition consisting essentially of a suitable pharmaceutical carrier and an effective antiinflammatory amount of a compound of claim 3.
13. A pharmaceutical composition consisting essentially of a suitable pharmaceutical carrier and an effective antiinflammatory amount of a compound of claim 4.
14. A pharmaceutical composition consisting essentially of a suitable pharmaceutical carrier and an effective antiinflammatory amount of a compound of claim 5.
15. A pharmaceutical composition consisting essentially of a suitable pharmaceutical carrier and an effective antiinflammatory amount of a compound of claim 6.
16. A pharmaceutical composition consisting essentially of a suitable pharmaceutical carrier and an effective antiinflammatory amount of the compound of claim 7.
17. A pharmaceutical composition consisting essentially of a suitable pharmaceutical carrier and an effective antiinflammatory amount of a compound of claim 8.
18. A pharmaceutical composition consisting essentially of a suitable pharmaceutical carrier and an effective antiinflammatory amount of the compound of claim 9.
19. A method of treating arthritis in a mammal which comprises administering to the mammal an effective antiarthritic amount of a compound of claim 1.
20. A method of treating arthritis in a mammal which comprises administering to the mammal an effective antiarthritic amount of a compound of claim 2.
21. A method of treating arthritis in a mammal which comprises administering to the mammal an effective antiarthritic amount of a compound of claim 3.
22. A method of treating arthritis in a mammal which comprises administering to the mammal an effective antiarthritic amount of a compound of claim 4.
23. A method of treating arthritis in a mammal which comprises administering to the mammal an effective antiarthritic amount of a compound of claim 5.
24. A method of treating arthritis in a mammal which comprises administering to the mammal an effective antiarthritic amount of a compound of claim 6.
25. A method of treating arthritis in a mammal which comprises administering to the mammal an effective antiarthritic amount of a compound of claim 7.
26. A method of treating arthritis in a mammal which comprises administering to the mammal an effective antiarthritic amount of the compound of claim 8.
27. A method of treating arthritis in a mammal which comprises administering to the mammal an effective antiarthritic amount of the compound of claim 9.

* * * * *